United States Patent [19]

Ryan

[11] Patent Number: 5,270,208

[45] Date of Patent: Dec. 14, 1993

[54] WHITE BLOOD CELL HEMATOLOGY CONTROL

[75] Inventor: Wayne L. Ryan, Omaha, Nebr.

[73] Assignee: Streck Laboratories, Inc., Omaha, Nebr.

[21] Appl. No.: 879,429

[22] Filed: May 7, 1992

Related U.S. Application Data

[63] Continuation-in-part of Ser. No. 697,331, May 9, 1991.

[51] Int. Cl.$^5$ .................. G01N 1/00; G01N 33/48
[52] U.S. Cl. .................. 436/10; 436/17; 436/18; 424/3; 252/408.1
[58] Field of Search ............ 436/8, 10, 13, 15–18, 436/63; 424/3; 252/408.1

[56] References Cited

U.S. PATENT DOCUMENTS

| | | | |
|---|---|---|---|
| 3,558,522 | 1/1971 | Louderback | 436/18 X |
| 3,873,467 | 3/1975 | Hunt | 436/10 |
| 4,219,440 | 8/1980 | Runck et al. | 252/408.1 |
| 4,299,726 | 11/1981 | Crews et al. | 436/10 |
| 4,324,687 | 4/1982 | Louderback et al. | 252/408.1 |
| 4,358,394 | 11/1982 | Crews et al. | 436/10 |
| 4,390,632 | 6/1983 | Carter, II | 436/17 X |
| 4,745,071 | 5/1988 | Lapicola et al. | 436/17 X |
| 4,777,139 | 10/1988 | Wong et al. | 436/17 X |

OTHER PUBLICATIONS

Lombarts, A.J.P.F. et al. "A White Blood Cell Control of Long-Term Stability" *Clinica Chimica Acta*, vol. 129, pp. 79–83 (1983).

Lombarts, A.J.P.F. et al. "A Stable Human Platelet–White Blood Cell Control for the Coulter Model S-Plus II" *Clinica Chimica Acta*, vol. 130, pp. 95–102 (1983).

*Primary Examiner*—James C. Housel
*Assistant Examiner*—Jeffrey R. Snay
*Attorney, Agent, or Firm*—Tilton, Fallon Lungmus & Chestnut

[57] ABSTRACT

Reference controls comprised of aldehyde-fixed white blood cells stabilized red blood cells and simulated blood platelets exhibiting a white blood cell histogram profile that is substantially that of whole blood are obtained by the addition of a lipoprotein to the control and an antioxidant to inhibit lysis of stabilized red blood cells by said lipoprotein.

15 Claims, 6 Drawing Sheets

WHITE BLOOD CELL HEMATOLOGY CONTROL

BACKGROUND OF THE INVENTION

This application is a continuation-in-part of U.S. application Ser. No. 07/697,331 filed May 9, 1991, pending, by Wayne L. Ryan.

FIELD OF THE INVENTION

The present invention relates to a method for preparing a hematology reference control and calibrator for hematology instruments used to measure granulocytes, lymphocytes, monocutes, eosinophiles and basophiles.

PRIOR ART

There are several hematology instruments which can analyze blood to determine the number of granulocytes, monocutes, lymphocytes, eosinophiles and basophiles. These instruments-include the coulter STKS, Unipath 3000, TOA NE 8000, TECHNICON H-1 and TECHNICON H-6000. Because these instruments employ different methods to measure the five populations of white cells, it has been necessary to employ a different type of reference control with each instrument. This fact has necessitated that the user stock separate controls for each of the types of instruments. From the user's standpoint, this situation is not only inconvenient, but can be expensive as well.

SUMMARY OF THE INVENTION

It is an object of the present invention to provide a reference control that can be used in a variety of hematology instruments.

It is a further object of the invention to provide a reference control that can be used for proficiency testing. Currently, when unknown samples are sent to laboratories to measure the proficiency of the laboratory to assay them, multiple samples are required. Because the control of the present invention is operative on all available instruments makes, it is possible to use a single control for testing all of the differential instruments.

The present invention provides a reference control for hematology instruments comprising:

i) white blood cells fixed with an aldehyde fixing agent suspended in an isotonic aqueous suspension medium; and ii) a composition comprising at least one lipoprotein in an amount sufficient to provide a mixture that gives a white blood cell histogram profile that is substantially the same as that of whole blood.

In a preferred embodiment, the aldehyde fixative comprises a mixture of formaldehyde and glutaraldehyde in a ratio of 3 to 20 ml formaldehyde: 0.01 to 1 ml of glutaraldehyde per 100 ml of fixing solution. As will be discussed below, the use of a mixture of formaldehyde and a small amount of glutaraldehyde reduces the amount of lipoprotein necessary to provide a histogram profile for fixed or stabilized white blood cell controls that is substantially the same as that of whole blood.

Particularly preferred reference controls of the invention further include predetermined amounts of both stabilized red blood cells and simulated blood platelets.

In another aspect of the invention, where the reference control includes stabilized red blood cells, it is advantageous to include in the reference control an antioxidant for the lipoprotein. It has been found that the lipoprotein component of the reference control has a tendency to cause lysing of the stabilized red blood cells. The mechanism by which the lipoprotein carries out the lysis is not known for certain but it is apparent the lysis is the result of an oxidation reaction. In any event, it has been found that the presence of an antioxidant in effective amounts will inhibit the lysis of the stabilized red cells. Any antioxidant can be employed as long as it does not adversely affect the desired function of the reference control. Illustrative of suitable antioxidants are ascorbic acid, butylated hydroxytoluene, Probucol (acetone bis (3, 5-di-test- butyl-4-hydroxyphenyl) mercaptole) bisphenabid, Rutin (Rutoside, quercetin-3-rutinoside), alpha-tocopherol, Deferoxamine Mesylate and Sulfasalazine.

The amounts of antioxidant employed will vary depending principally upon the particular antioxidant selected and the amount of lipoprotein employed. In general, however, the amount ranges from 0.1 to 100 mg/dl. More specifically, the following table sets forth amounts of the recited antioxidants that are normally employed:

| ANTIOXIDANTS USED WITH LIPOPROTEINS | | |
| --- | --- | --- |
| Antioxidants | Range of Use | Preferred |
| Ascorbic acid | 25-100 mg/dl | 50 mg/dl |
| Butylated hydroxytoluene | 1-10 mg/dl | 3 mg/dl |
| Probucol (acetone bis (3,5-di-tert-butyl-4-hydroxyphenyl) mercaptole) bisphenabid | 0.1-10 mg/dl | 3 mg/dl |
| Rutin (Rutoside, quercetin-3-rutinoside) | 0.001-0.01 mg/dl | 0.01 mg/dl |
| Alpha-tocopherol | 1-25 mg/dl | 3 mg/dl |
| Deferoxamine Mesylate | 30-500 mg/dl | 100 mg/dl |
| Sulfasalazine | 40-400 mg/dl | 200 mg/dl |

The invention also provides a method of preparing a stabilized reference control for hematology instruments comprising mixing white blood cells fixed with an aldehyde fixing agent, an isotonic aqueous suspension medium and at least one lipoprotein in an amount sufficient to provide a mixture that gives a white blood cell histogram profile that is substantially the same as that of blood.

In a preferred embodiment of the method, stabilized red blood cells and simulated platelets are mixed with the isotonic aqueous suspension, lipoprotein and an antioxidant to inhibit lysis of the stabilized red blood by the lipoprotein.

DETAILED DESCRIPTION OF THE INVENTION

Figure 1A:
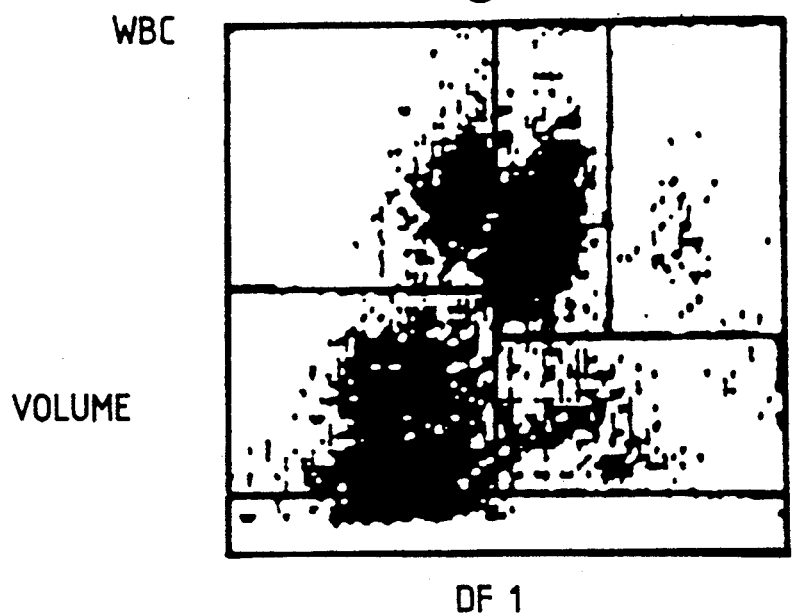
FIGS. 1A-1C illustrate a white blood cell histogram for whole blood. It is a goal of the invention to make a reference control which produces a histogram like that of FIG. 1.
Figure 1B:
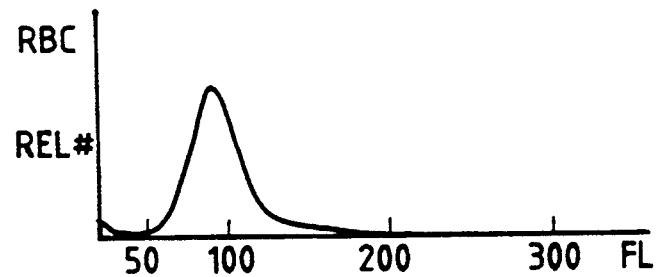
Figure 1C:
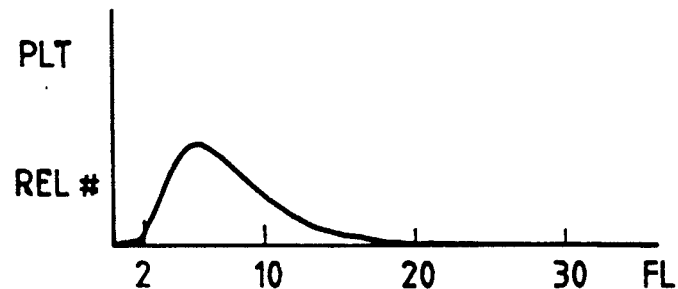
Figure 2A:
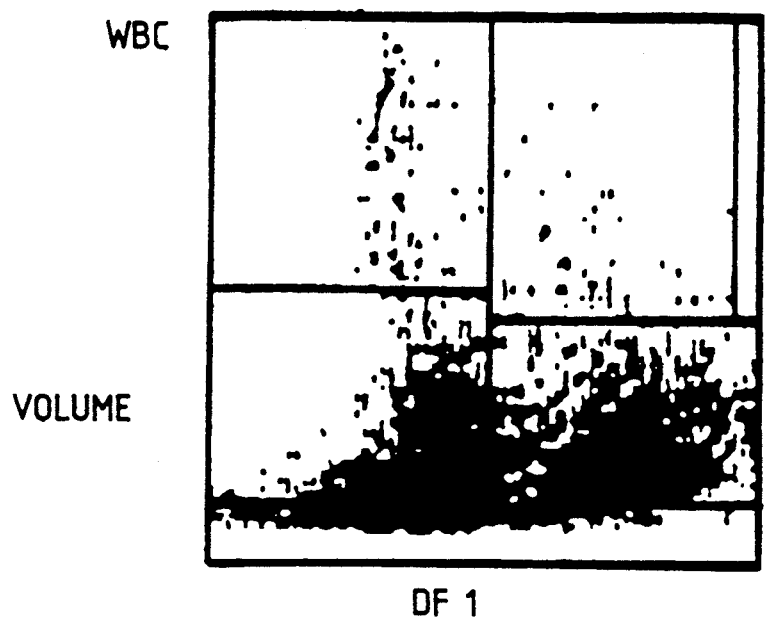
FIGS. 2A-2C is a white cell histogram made after washing the white cell component of FIG. 1 in an isotonic saline solution. This demonstrates the changes to the histogram of FIG. 1 caused by washing.
Figure 2B:
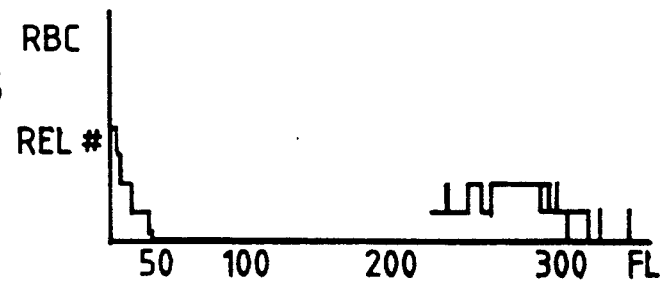
Figure 2C:
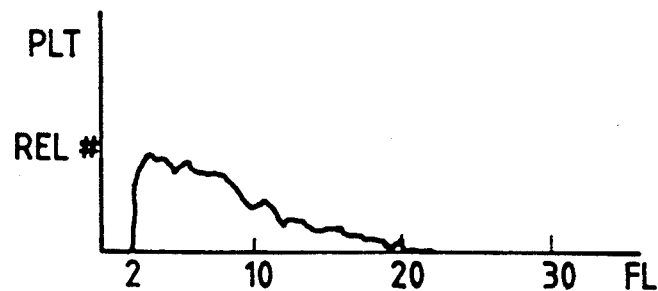

When fresh whole blood samples are collected, they contain five different white cell subpopulations, four of which can be seen in the histogram in FIGS. 1 and 2 obtaining using a Coulter STKS. The four visible populations are monocytes 10, neutrophiles 12, eosonophiles 14 and lymphocytes 16.

Figure 5A:
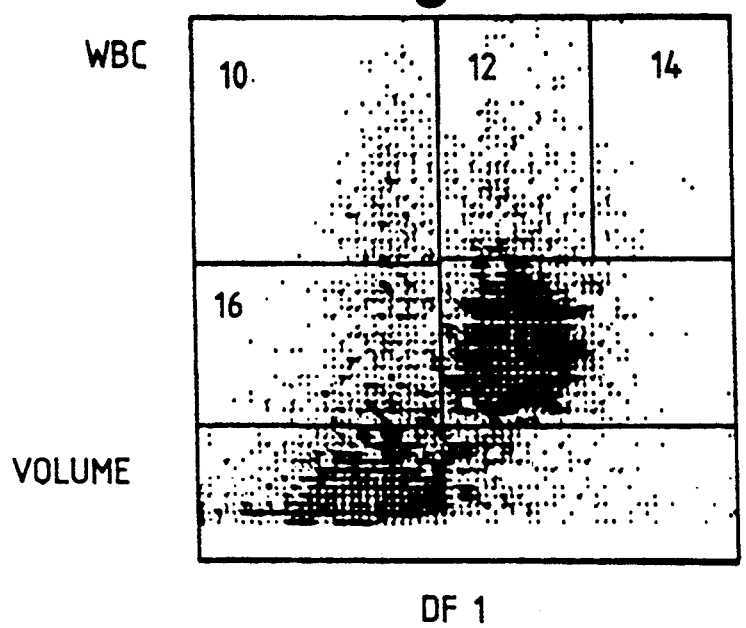
FIG. 5A-5C illustrate the effect on the histogram for washed and fixed white cells showing the variation from FIG. 1.
Figure 5B:
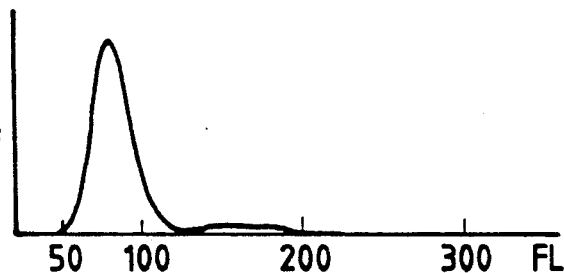
Figure 5C:
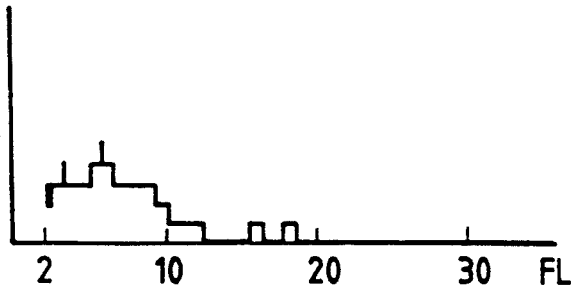

When these subpopulations of white blood cells are separated from whole blood as, for instance, by differential centrifugation, washed with isotonic saline and used to prepare a reference control, the histogram of the resulting control is different in appearance from that of whole blood. In fact, the more the white blood cells are washed the more the histogram changes. A change in a white blood cell histogram due to washing is shown in FIG. 2. From these experiments it is clear that something responsible for the proper positioning in the histogram of white cell subpopulations is being removed. Similarly, when histograms are taken of reference controls made up of white blood cells washed and fixed with aldehyde fixing agents, the result is again an improper positioning of white blood cell subpopulations. (See FIG. 5)

It has been unexpectedly found that the addition of an effective amount of a composition comprising at least one lipoprotein to an aqueous isotonic suspension of aldehyde fixed white blood cells gives a histogram profile that is substantially that of whole blood. The finding was particularly surprising since other proteins have little effect on the positioning of the white blood cell populations. For example, reference samples containing commercially available proteins such as albumin, alpha-globulin, beta-globulin, gamma-globulin and fibronogen were tested and found to have an insignificant effect on the positioning.

Figure 3A:
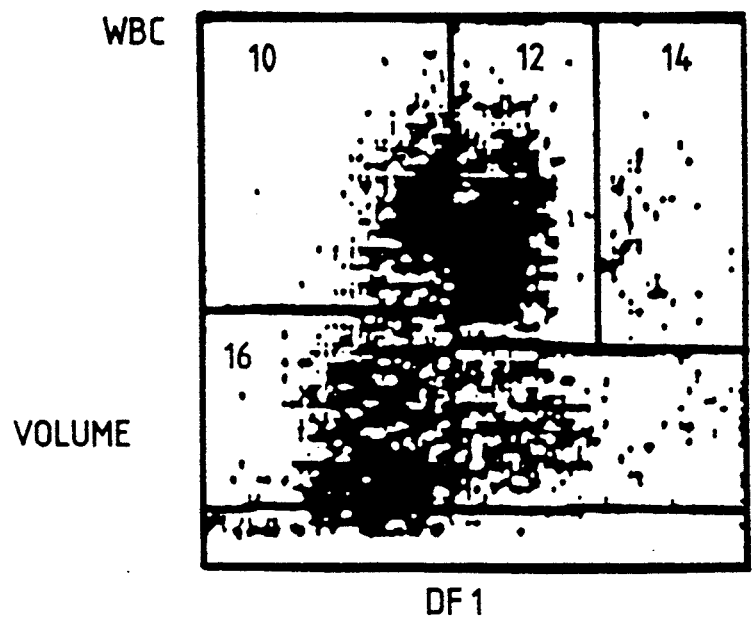
FIGS. 3A-3C show that the histogram for washed white cells (as in FIG. 2) will look more like FIG. 1 after treatment with concentrated serum.
Figure 3B:
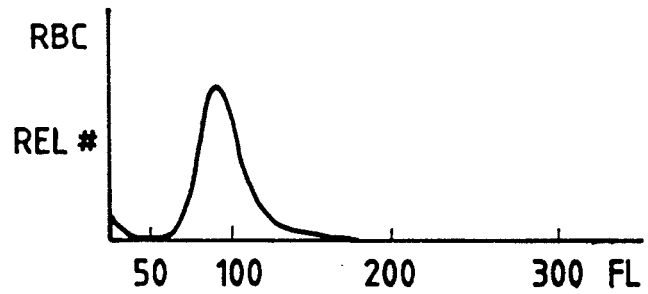
Figure 3C:
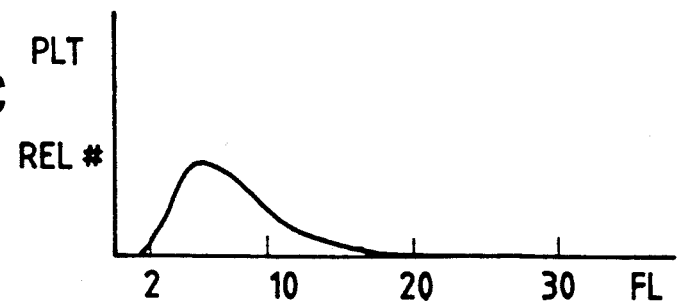
Figure 4A:
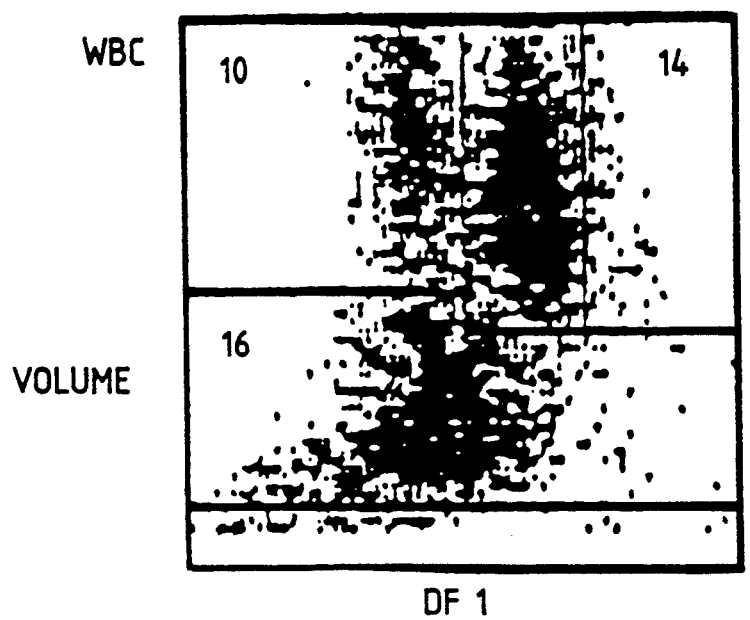
FIGS. 4A-4C show that the histogram for washed white cells (as in FIG. 2) will look more like FIG. 1 after treatment with concentrated plasma solution.
Figure 4B:
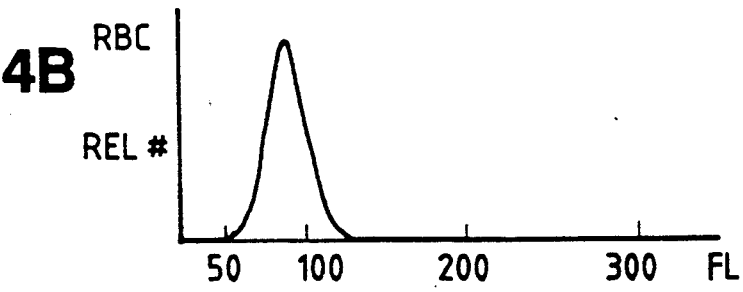
Figure 4C:
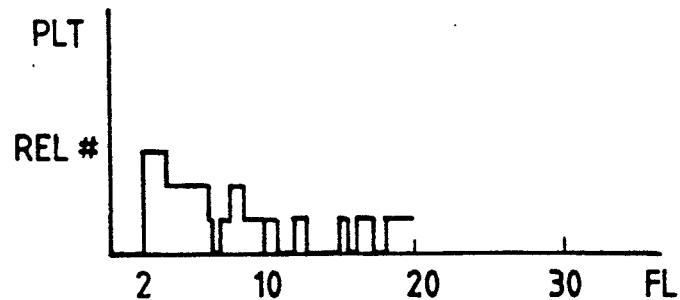

The lipoproteins suitable for use in the present invention can be either high or low density lipoproteins, both of which are available from a number of commercial sources. Lipoproteins from the serum of various animals, (e.g. horse and bovine) and egg yolk lipoprotein all have been found to exhibit the desired effect. (See FIG. 6) It is also possible to use compositions containing lipoproteins as the lipoprotein source. Examples of such lipoprotein sources are animal (include man) blood serums and plasmas. (See FIG. 3 and FIG. 4) Where such lipoprotein-containing compositions are employed, the amount of composition employed in the reference controls of the invention will depend upon the concentration of the lipoprotein. Preferred blood plasma or serum concentrates are those concentrated two to three fold so as to contain about 14 to 17% by weight of protein.

As aforementioned, the amount of lipoprotein added to the stabilized white blood cells is that which effectively moves the white blood cell subpopulations in the histogram to the correct position, i.e. so that the histogram to substantially mimics the white blood cell histogram for whole blood. Generally, the amount of lipoprotein in the final product will vary from about 0.5 to 8.0% by volume, depending upon the type of lipoprotein used. For example, two to three times more low density protein is required than high density lipoproteins. When egg lipoproteins are used about 30% more is necessary than high density lipoprotein.

The aqueous suspension medium employed in the reference control of the invention is one that is nondeleterious to the white blood cells and, optionally, red blood cells or platelets to be counted. The suspension medium is preferably a physiological salt solution such as an isotonic salt solution, advantageously buffered to a pH neutral to alkaline, preferably a pH of 7 to 9. Preferred buffering agents include alkali metal phosphates such as disodium phosphate, monopotassium phosphate, monosodium phosphate, sodium citrate and the like and mixtures thereof.

The white blood cells of the reference control of the invention are fixed with an aldehyde fixing agent to partially rigidify their cell membranes and render them stable. Aldehyde fixing agents for white blood cells are well known and include, for instance, formaldehyde and glutaraldehyde. The fixatives are preferably prepared in phosphate buffered saline. The amount of aldehyde employed in the fixatives will vary depending upon the particular aldehyde employed but normally falls in the range of about 1 to 20% by volume of fixing agent. The preferred fixative is a mixture of formaldehyde and glutaraldehyde in a ratio of 0.01 to 1.0 ml of glutaraldehyde; 3 to 20 ml formaldehyde per 100 ml of fixative. It has been discovered that reference controls made up of white blood cells fixed with the mixture of formaldehyde and glutaraldehyde require less lipoprotein to properly position the white blood cells. The presence of a small amount of glutaraldehyde decreases the amount of lipoprotein required.

Advantageously, the reference control of the invention may also include stabilized red blood cells and simulated blood platelets commonly employed in prior art reference controls in a number, size, and distribution equal to that of human whole blood. Suitable simulated blood platelets are described in U.S. Pat. Nos. 4,436,821 and 4,160,644 hereby incorporated by reference. The red blood cells can be stabilized by treatment with aldehyde prior to suspension in the isotonic suspension medium or alternatively by incorporating stabilizing additives in the isotonic suspension. Illustrative of prior art methods for stabilizing or fixing red blood cells include those described in U.S. Pat. Nos. 4,358,394; 4,299,726; 3,873,467; 4,390,632; 4,698,726 and 4,777,139, all hereby incorporated by reference.

The invention will now be further described with reference to the examples below.

EXAMPLE 1

Human white blood cells are obtained as concentrates from commercial blood banks. The white blood cells are washed and freed of red blood cells by placing in trisammonium chloride buffer for several minutes. Trisammonium chloride and 20 ml Trizma base (tris (hydroxy methyl) amino methan) to one liter of distilled water. The white blood cells are stabilized by adding phosphate buffered saline containing 13 ml of 37% formaldehyde/100 ml of phosphate buffered saline. The cells are held in the fixative for 24 hours and then washed with phosphate buffered saline. The white blood cells are added to a red cell preservative diluent containing lipoprotein. The amount of lipoprotein varies with the purity and type used. The commercial preparation used is Mules SUPERTRATE and it is used at 0.5-5% v/v.

This mixture of blood cells and lipoprotein result in a stable control that produces a histogram similar to whole blood on the COULTER STK-S, TOA NE-8000, TECHNICON H-1, TECHNICON H-6000, and the CEL-DYN 3000.

EXAMPLE 2

White blood cells are fixed with 37% formaldehyde diluted to 20% v/v in phosphate buffered saline containing 0.33 ml of 25% glutaraldehyde. After fixing for 24 hours the cells are washed with saline and added to red cells in a stabilizing solution containing sodium citrate, magnesium gluconate and antibiotics. After adding the white blood cells, simulated platelets prepared as described in U.S. Pat. No. 4,160,644 are added.

The simulated platelets and the white blood cells are added to the red cells in the stabilizing diluent at normal, high abnormal and low abnormal levels. Finally lipoprotein (Supertrate Miles—a high density lipoprotein >70%, protein 5.8, 48–49 dynes/cm$^2$) is added at a concentration of 2% v/v (0.5–5.0%).

Figure 6A:
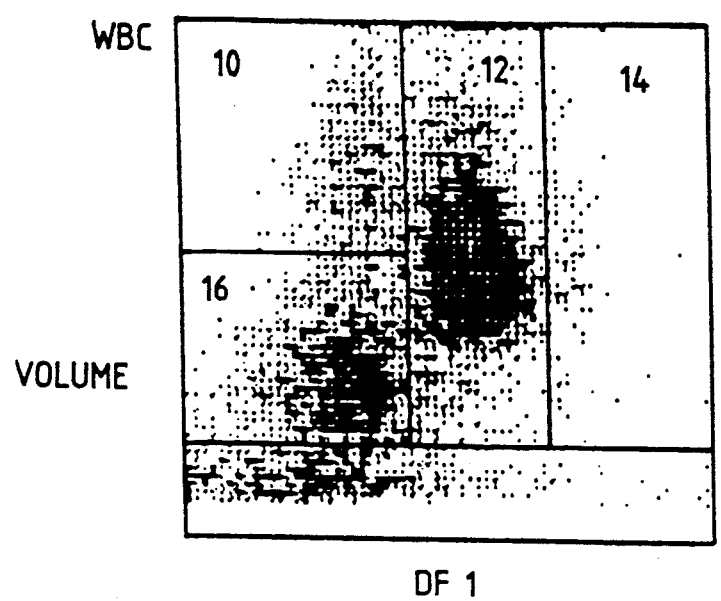
FIGS. 6A-6C show the histogram for the reference control of the invention. It illustrates the effectiveness of the invention in producing a histogram similar to FIG. 1. The reference control for the invention provides a 5-part differential on the TOA NE-8000, TECHNICON H-1, TECHNICON H-6000, CEL-OYN 3000 as well as the Coulter STKS.
Figure 6B:
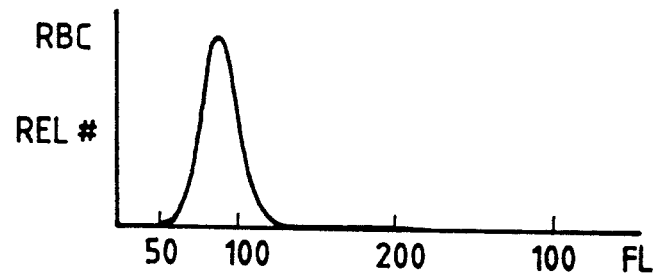
Figure 6C:
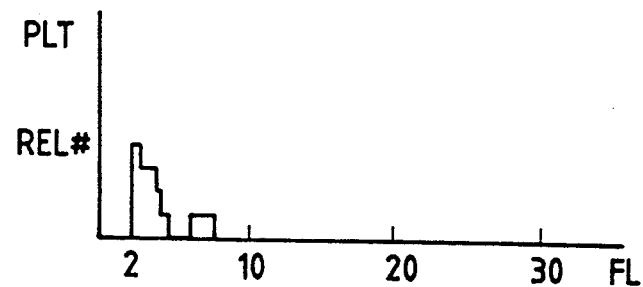

Example of final values for normal level control:
red blood cells—$4.75 \times 10^6$/mm$^3$
white blood cells—$8 \times 10^3$/mm$^3$
Platelets—$225 \times 10^3$/mm$^3$ FIG. 6 shows a histogram on STKS of the completed product. This product also provides a 5-part differential on the TOA NE-8000, TECHNICON H-1, TECHNICON H-6000, CEL-DYN 3000 as well as the STKS.

A mixture of formaldehyde and glutaraldehyde used a fixative is preferred because it decreases the amount of lipoprotein required to produce a white cell histogram which substantially mimics the white cell histogram for whole blood.

EXAMPLES 3–9

Example 2 is repeated adding the following antioxidants to the stabilizing solution in the designated amounts:

| Example | Antioxidant |
| --- | --- |
| 3 | Ascorbic acid |
| 4 | Butylated hydroxytoluene |
| 5 | Deferoxamine Mesylate |
| 6 | acetone bis (3,5-di-tert-butyl-4-hydroxyphenyl) mercaptole) bisphenabid |
| 7 | Rutin (Rutoside, quercetin-3-rutinoside) |
| 8 | Alpha-tocopherol |
| 9 | Sulfasalazine |

In each of Examples 3–9, the antioxidants is effective in inhibiting lysis of the red blood cells.

It is claimed:

1. A reference control for hematology instruments comprising:
   i) white blood cells fixed with an aldehyde fixing agent, stabilized red blood cells and simulated blood platelets, suspended in an isotonic aqueous suspension medium,
   ii) a composition comprising at least one lipoprotein in an amount sufficient to provide a mixture that gives a white blood cell histogram profile that is substantially that of whole blood, and
   iii) an antioxidant in an amount effective to inhibit lysis of said stabilized red blood cells.

2. The reference control of claim 1, wherein the suspension solution comprises buffered saline solution.

3. The reference control of claim 1, wherein the lipoprotein is a high density lipoprotein.

4. The reference control solution of claim 1 wherein said fixing agent comprises a mixture of formaldehyde and glutaraldehyde in a ratio of 3 to 15 ml formaldehyde: 0.01 to 1 ml of glutaraldehyde per 100 ml of fixing solution.

5. The reference control of claim 4, wherein the amount of lipoprotein is 0.5 to 8% by volume.

6. The reference control of claim 1, wherein the lipoprotein is added in the form of a concentrated blood serum or plasma.

7. The reference control of claim 1 wherein the antioxidant is alpha-tocopherol.

8. The reference control of claim 1 wherein the antioxidant is selected from the group consisting of:

| | |
| --- | --- |
| Ascorbic acid at | 25–100 mg/dl, |
| Butylated hydroxytoluene at | 1–10 mg/dl, |
| Probucol (acetone bis (3,5-di-tert-butyl-4-hydroxyphenyl) mercaptole) bisphenabid at | 0.1–10 mg/dl, |
| Rutin (Rutoside, quercetin-3-rutinoside) at | 0.001–0.01 mg/dl, |
| Alpha-tocopherol at | 1–25 mg/dl, |
| Deferoxamine Mesylate at | 30–500 mg/dl, and |
| Sulfasalazine at | 40–400 mg/dl. |

9. A method for making a reference control for hematology instruments comprising mixing white blood cells fixed with an aldehyde fixing agent, stabilized red blood cells and simulated blood platelets in an isotonic aqueous suspension medium with at least one lipoprotein in an amount sufficient to provide a mixture that gives a white blood cell histogram profile that is substantially the same as that of blood, and an antioxidant in an amount effective to inhibit lysis of said stabilized red blood cells.

10. The method of claim 9, wherein the suspension solution comprises buffered saline solution.

11. The method of claim 9, wherein lipoprotein is a high density lipoprotein.

12. The method of claim 9, wherein said fixing agent comprises a mixture of formaldehyde and glutaraldehyde in a ratio of 3 to 20 ml formaldehyde: 0.01 to 1 ml of glutaraldehyde per 100 ml of fixing solution.

13. The method of claim 12, wherein the amount of lipoprotein is 0.5 to 8% by volume.

14. The method of claim 9, wherein the lipoprotein is added in the form of a concentrated blood serum or plasma.

15. The method of claim 9, wherein the antioxidant is selected from the group consisting of:

| | |
| --- | --- |
| Ascorbic acid at | 25–100 mg/dl, |
| Butylated hydroxytoluene at | 1–10 mg/dl, |
| Probucol (acetone bis (3,5-di-tert-butyl-4-hydroxyphenyl) mercaptole) bisphenabid at | 0.1–10 mg/dl, |
| Rutin (Rutoside, quercetin-3-rutinoside) at | 0.001–0.01 mg/dl, |
| Alpha-tocopherol at | 1–25 mg/dl, |
| Deferoxamine Mesylate at | 30–500 mg/dl, and |
| Sulfasalazine at | 40–400 mg/dl. |

* * * * *